US005882869A

United States Patent [19]

Potter et al.

[11] Patent Number: 5,882,869

[45] **Date of Patent: *Mar. 16, 1999**

[54] PLANT ADENYLOSUCCINATE SYNTHETASE AND DNA CODING THEREFOR

[76] Inventors: Sharon Lee Potter, 3837 Whispering Branch Rd., Raleigh, N.C. 27613; Eric R. Ward, Säckingerstrasse 20, CH-4058, Basel, Switzerland

[ * ] Notice: The term of this patent shall not extend beyond the expiration date of Pat. Nos. 5,519,125 and 5,688,939.

[21] Appl. No.: 946,967

[22] Filed: Oct. 8, 1997

Related U.S. Application Data

[60] Continuation of Ser. No. 612,033, Mar. 7, 1996, abandoned, which is a division of Ser. No. 361,611, Dec. 22, 1994, Pat. No. 5,519,125.

[51] Int. Cl.[6] .............................. C12P 1/68; C12Q 19/34; C07H 21/02; C07H 21/04

[52] U.S. Cl. ............................ 435/6; 435/91.2; 536/24.3; 536/24.33; 935/77; 935/78

[58] Field of Search ..................... 435/6, 91.2; 536/24.3, 536/24.33; 935/77, 78

*Primary Examiner*—Stephanie W. Zitomer
*Attorney, Agent, or Firm*—Larry W. Stults

[57] ABSTRACT

The present invention provides novel plant DNA sequences coding for native adenylosuccinate synthetase (ADSS). Methods for using the complete or partial ADSS coding sequence as a probe for diagnostic, mapping and other purposes are taught. Generation of transformed host cells capable of expressing ADSS is also taught. Methods of using the transformed host cells are taught, including methods for recombinant production of ADSS enzymes. A method for using the plant ADSS enzyme to screen for inhibitors of ADSS activity is also provided.

8 Claims, No Drawings

PLANT ADENYLOSUCCINATE SYNTHETASE AND DNA CODING THEREFOR

This is a continuation of Ser. No. 08/612,033, filed Mar. 7, 1996, now abandoned, which is a divisional of Ser. No. 08/361,611, filed, Dec. 22, 1994, issued as U.S. Pat. No. 5,519,125.

FIELD OF THE INVENTION

The invention relates generally to an enzymatic activity involved in adenosine 5'-monophosphate biosynthesis in plants. In particular, the invention relates to the plant enzyme which catalyzes the synthesis of adenylosuccinate and the gene encoding this enzyme. In one aspect, the invention relates to the recombinant production of this enzyme in a heterologous host. In another aspect, the invention is applied to the identification of new herbicides. In yet another aspect, the invention relates to the development of genetic markers in plants.

BACKGROUND OF THE INVENTION

Adenosine 5'-monophosphate (AMP, also known as adenylic acid) is a precursor of adenosine 5'-triphosphate (ATP), the key energy carrying molecule for all living systems. The first committed enzymatic step in the biosynthesis of AMP is the synthesis of adenylosuccinate from inosine 5'-monophosphate (IMP; inosinic acid) and aspartate. The enzyme which catalyzes this step is known as adenylosuccinate synthetase (IMP:L-aspartate ligase(GDP-forming), EC 6.3.4.4, referred to herein as "ADSS").

In *E. coli,* ADSS is a dimer of identical 48 kD subunits. Its three-dimensional structure has been determined to 2.8 Å resolution (Poland et al., *J Biol. Chem.* 268:25334–25342 (1993). In mammalian cells, the ADSS enzyme is present as two isoforms. An acidic form, present in non-muscle tissues, is thought to be involved in de novo production of AMP. A basic form, present in muscle tissue, thought to act as part of the purine nucelotide cycle, which involves interconversion of IMP and AMP with the net result of deaminating aspartate to fumarate (Lehninger, *Biochemistry*. Worth Publishers, NY (1975), p. 743; Lowenstein, *Int. J. Sports Med.*11: S36–S46 (1990).

Genes encoding the ADSS enzyme have been isolated from a variety of species including *E. coli* (Wolfe and Smith, *J. Biol. Chem.* 263: 19147–19153 (1988)), *D. discoideum* (Weismuller et al., *J Biol. Chem.* 266: 2480–2485 (1991)), mouse (Guicherit et al., *J Biol. Chem.* 266: 22582–22587 (1991); Guicherit et al., *J. Biol. Chem.* 269: 4488–4496 (1994), *Bacillus subtilus* (Maentsaelae and Zalkin, *J. Bacteriol.* 174: 1881–1890 (1992), human (Powell et al., *FEBS Lett.* 303: 4–10 (1992), *S. cerevisiae* (Genbank accession no. L22185), and *Caenorhabditis elegans* (EST; Genbank accession no. M75738). However, genes encoding the ADSS enzyme have heretofore not been isolated from any plant species.

Presently, too little is known about the plant ADSS enzyme and its relationship to the ADSS enzymes/genes which have been isolated from other organisms to allow isolation of ADSS encoding genes from any plant species using known approaches.

Methods for isolating genes which are based upon knowledge of the structure of the proteins they encode cannot be applied to plant ADSS genes because too little is presently known about plant ADSS enzymes. Metabolic enzymes such as ADSS are typically very difficult to purify from plants because of their extremely low abundance. In addition, the presence of various phenolic and carbohydrate compounds in plants can interfere with the isolation of pure enzyme with native activity.

In the absence of direct structural information, a number of standard techniques are available for the isolation of proteins and their corresponding genes. Such standard techniques include nucleic acid hybridization and amplification by polymerase chain reaction using oligonucleotide primers corresponding to conserved amino acid sequence motifs. Unfortunately, these techniques would not be expected to be useful for isolation of plant ADSS genes because they rely upon the presence of significant structural similarity (i.e. amino acid and DNA sequence) with known proteins and genes that have the same function. Since there is no significant structural similarity even among the known ADSS genes and proteins from non-plant organisms (see, e.g. Powell et al., *FEBS Lett.* 303: 4–10 (1992)) it is unlikely that these proteins would share any significant structural similarity with plant ADSS proteins.

Another approach that has been used to isolate biosynthetic genes in other metabolic pathways from higher eukaryotes is the complementation of microbial mutants deficient in the activity of interest. For this approach, a library of cDNAs from the higher eukaryote is cloned in a vector that can direct expression of the cDNA in the microbial host. The vector is then transformed or otherwise introduced into the mutant microbe, and colonies are selected that are phenotypically no longer mutant.

This strategy has worked for isolating genes from higher eukaryotes that are involved in several metabolic pathways, including histidine biosynthesis (e.g. U.S. patent application Ser. No. 08/061,644 to Ward et al., incorporated by reference herein in its entirety), lysine biosynthesis (e.g. Frisch et al., *Mol. Gen. Genet.* 228: 287 (1991)), purine biosynthesis (e.g. Aimi et al., *J Biol. Chem.* 265: 9011 (1990)), and tryptophan biosynthesis (e.g. Niyogi et al., *Plant Cell* 5: 1011 (1993)). This strategy has also been used to isolate plant genes including those coding for maize glutamine synthase (Snustad et al, *Genetics* 120:1111–1114 (1988)), soybean-pyrroline-5-carboxylate reductase (Delauney et al., *Mol. Genet.* 221:299–305 (1990), maize dihydrodipicolinate synthase (Frisch et al., *Mol. Gen. Genet.* 228:287–293(1991)), rape chloroplast 3-isopropylmalate dehydrogenase (Eller et al., *Plant Mol. Biol.* 18:557–566 (1992); *Proc. Natl. Acad. Sci, USA* 88:1731–1735 (1991)), and dihydroorotate dehydrogenase (Minet et al., *Plant J.* 2:417–422 (1992)).

Microbial mutants thought to be defective in ADSS activity are available (e.g. *E. coli* purA mutant designated CGCS 5408 and *E. coli* strains CGCS 4431 and 7039 from *E. coli* Genetic Stock Center, Yale Univ.; yeast ade 12 mutants reported in Dorfman, *Genetics* 61:377–389 (1969)). However, despite the availability of these mutants, application of the complementation technique to isolate cDNAs encoding ADSS enzymatic activity has proven to be unsuccessful for avian (Powell et al, *FEBS Lett.* 303: 4–10 (1992)) and *B. subtilis* ADSS (Maentsaelae and Zalkin, *J. Bacteriol.* 174: 1881–1890 (1992).

There are several reasons which may explain the failure of this complementation strategy when applied to ADSS, particularly eukaryotic ADSS genes. First, the eukaryotic ADSS cDNA sequence may not be expressed at adequate levels in the mutant microbe, for instance because of codon usage inconsistent with the usage preferences of the microbial host. Second, the primary translation product from the cloned eukaryotic coding sequence may not produce a functional polypeptide, for instance if activity requires a post-translational modification, such as glycosylation, that is not carried out by the microbe. Third, the heterologous protein expressed in *E. coli* may also be lethal to the cells in which it is expressed, thus rendering its isolation impossible. Fourth, the eukaryotic protein may fail to assume its active conformation in the microbial host, for instance if the protein is normally targeted to a specific organellar membrane system that the microbial host specifically lacks. This last possibility is especially likely for the plant ADSS enzyme, which has been associated in the plant cell with organelles not present in microbial hosts used in the complementation assay (Schubert, *Annu. Rev. Plant Physiol.* 37:539–574 (1986), and presumably reaches that organellar system as a result of a post-translational targeting mechanism involving both an N-terminal transit sequence, and intrinsic properties of the mature polypeptide (see, e.g. Kohorn and Tobin, *Plant Cell* 1: 159 (1989); Li et al., *Plant Cell* 3: 709 (1991); Li et al., *J. Biol. Chem.* 267: 18999 (1992)). Moreover, two other purine biosynthetic genes isolated from plants, 5'-phosphoribosyl-5-aminoimdazole synthetase (Senecoff and Meagher, *Plant Physiol.* 102:387–399 (1993)) and glycinamide synthetase (Schnorr et al., *Plant J.* 6:113–121 (1994)) also appear encode proteins that are targeted to the chloroplast.

SUMMARY OF THE INVENTION

The present invention provides an isolated DNA molecule encoding the adenylosuccinate synthetase (ADSS) enzyme from a plant source.

The DNA coding sequences for ADSS enzymes in *Arabidopsis thaliana* and *Zea mays* are provided in SEQ ID NOS: 1 and 3, respectively. Using the information provided by the present invention, the DNA coding sequence for the adenylosuccinate synthetase (ADSS) enzyme from any plant source may now be obtained using standard methods.

The present invention also encompasses the recombinant production of the ADSS enzyme, and methods for using recombinantly produced ADSS. In particular, the present invention provides methods of using purified ADSS to screen for novel herbicides which affect the activity of ADSS.

The present invention is further directed to probes and methods for detecting the presence and form of the ADSS gene and quantitating levels of ADSS transcripts in an organism. These methods may be used to diagnose disease conditions which are associated with an altered form of the ADSS enzyme or altered levels of expression of the ADSS enzyme.

DETAILED DESCRIPTION OF THE INVENTION

In one aspect, the present invention is directed to an isolated DNA molecule which encodes a eukaryotic form of adenylosuccinate synthetase (referred to herein as "ADSS"), the enzyme which catalyzes the synthesis of adenylosuccinate from IMP. The DNA coding sequence and corresponding amino acid sequence for an ADSS enzyme from *Arabidopsis thaliana* is provided as SEQ ID NOS:1 and 2, respectively. The DNA coding sequence and corresponding amino acid sequence for a maize ADSS enzyme is provided as SEQ ID NOS:3 and 4, respectively.

The DNA encoding the ADSS enzyme may be isolated from the genome of any plant species desired according to the invention. One method taught for isolating a plant ADSS coding sequence is represented by Example 1. In this method cDNA clones encoding an ADSS enzyme are identified from a library of cDNA clones derived from the eukaryote of interest based on their ability to supply ADSS enzymatic activity to a mutant host organism deficient in this activity. Suitable host organisms for use in this method are those which can be used to screen cDNA expression libraries and for which mutants deficient in ADSS activity are either available or can be routinely generated. Such host organisms include, but are not limited to, *E. coli* and yeast.

Alternatively, plant ADSS coding sequences may be isolated according to well known techniques based on their sequence homology to the *Arabidopsis thaliana* (SEQ ID NO:1) and *Zea mays* (SEQ ID NO:3) ADSS coding sequences taught by the present invention. In these techniques all or part of the known ADSS coding sequence is used as a probe which selectively hybridizes to other ADSS coding sequences present in population of cloned genomic DNA fragments or cDNA fragments (i.e. genomic or cDNA libraries) from a chosen organism. Such techniques include hybridization screening of plated DNA libraries (either plaques or colonies; see, e.g. Sambrook et al., "Molecular Cloning", eds., Cold Spring Harbor Laboratory Press. (1989)) and amplification by PCR using oligonucleotide primers corresponding to sequence domains conserved among known ADSS amino acid sequences (see, e.g. Innis et al., "PCR Protocols, a Guide to Methods and Applications", pub. by Academic Press (1990)). These methods are particularly well suited to the isolation of ADSS coding sequences from organisms closely related to the organism from which the probe sequence is derived. Thus, application of these methods using the Arabidopsis or *Zea mays* coding sequence as a probe would be expected to be particularly well suited for the isolation of ADSS coding sequences from other plant species.

The isolated plant ADSS sequences taught by the present invention may be manipulated according to standard genetic engineering techniques to suit any desired purpose. For example, the entire ADSS sequence or portions thereof may be used as probes capable of specifically hybridizing to ADSS coding sequences and messenger RNAs. To achieve specific hybridization under a variety of conditions, such probes include sequences that are unique among ADSS coding sequences and are preferably at least 10 nucleotides in length, and most preferably at least 20 nucleotides in length. Such probes may be used to amplify and analyze ADSS coding sequences from a chosen organism via the well known process of polymerase chain reaction (PCR). This technique may be useful to isolate additional ADSS coding sequences from a desired organism or as a diagnostic assay to determine the presence of ADSS coding sequences in an organism. This technique may also be used to detect the presence of altered ADSS coding sequences in a plant associated with a particular condition of interest such as herbicide resistance, AMP deficiency, poor health, etc.

ADSS specific hybridization probes may also be used to map the location of the native ADSS gene(s) in the genome of a chosen plant using standard techniques based on the selective hybridization of the probe to genomic ADSS sequences. These techniques include, but are not limited to, identification of DNA polymorphisms identified or contained within the ADSS probe sequence, and use of such polymorphisms to follow segregation of the ADSS gene relative to other markers of known map position in a mapping population derived from self fertilization of a hybrid of two polymorphic parental lines (see e.g. Helentjaris et al., *Plant Mol. Biol.* 5: 109 (1985); Sommer et al. *Biotechniques* 12:82 (1992); D'Ovidio et al., *Plant Mol.*

*Biol.* 15: 169 (1990)). While any plant ADSS sequence is contemplated to be useful as a probe for mapping ADSS genes, preferred probes are those ADSS sequences from plant species more closely related to the chosen plant species, and most preferred probes are those ADSS sequences from the chosen plant species. Mapping of ADSS genes in this manner is contemplated to be particularly useful for breeding purposes. For instance, by knowing the genetic map position of a mutant ADSS gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of ADSS-linked flanking chromosomal DNA still present in the recurrent parent after each round of back-crossing.

ADSS specific hybridization probes may also be used to quantitate levels of ADSS mRNA in a plant using standard techniques such as Northern blot analysis. This technique may be useful as a diagnostic assay to detect altered levels of ADSS expression that may be associated with particular conditions such as deficiencies in adenylosuccinate or AMP levels or enhanced tolerance to herbicides which target ADSS.

For recombinant production of the enzyme in a host organism, the plant ADSS coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pV111392/Sf21 cells (Invitrogen, La Jolla, Calif.).

Recombinantly produced plant ADSS enzyme can be isolated and purified using a variety of standard techniques. The actual techniques which may be used will vary depending upon the host organism used, whether the ADSS enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced plant ADSS enzyme is useful for a variety of purposes. For example, it may be used to supply ADSS enzymatic activity in vitro to synthesize adenylosuccinate. In vitro synthesis of adenylosuccinate may be accomplished by reacting IMP, GTP, and aspartate in the presence of ADSS enzyme in an appropriate buffer, containing a divalent cation such as $Mg^{2+}$ (see, e.g. Baugher et al. *Biochem. Biophys. Res. Commun.* 94:123–129 (1980); Stayton et al. *Curr. Top. Cell. Regul.* 22.103–141 (1983); Bass et al., *Arch. Biochem. Biophys*. 256:335–342 (1987)). The adenylosuccinate produced is a useful reagent which may be used as a substitute for purified adenylosuccinic acid previously available commercially from other sources.

Recombinantly produced plant ADSS enzyme may also be used in an in vitro assay to screen known herbicidal chemicals whose target has not been identified to determine if they inhibit ADSS. Such an in vitro assay may also be used as a more general screen to identify chemicals which inhibit ADSS activity and which are therefore herbicide candidates. Alternatively, recombinantly produced ADSS may be used to elucidate the complex structure of this enzyme. Such information regarding the structure of the ADSS enzyme may be used, for example, in the rational design of new inhibitory herbicides.

Typically, the inhibitory effect on ADSS is determined by a reduction or complete inhibition of adenylosuccinate synthesis in the in vitro assay (see, e.g. Baugher et al. *Biochem. Biophys. Res. Commun.* 94:123–129 (1980); Stayton et al. *Curr. Top. Cell. Regul.* 22:103–141 (1983); Bass et al., *Arch. Biochem. Biophys*. 256:335–342 (1987)). Such a determination may be made simply by comparing the amount of adenylosuccinate synthesized in the in vitro assay in the presence and absence of the candidate inhibitor.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Isolation of Arabidopsis cDNAs encoding ADSS genes by functional complementation of an *E. coli* mutant.

An *Arabidopsis thaliana* (Landsberg) cDNA library in the plasmid vector pFL61 (Minet et al., *PlantJ*. 2:417–422 (1992)) was obtained and amplified. The *E. coli* purA mutant PC0543 (CGSC #5408; *E. coli* Genetics Stock Center, Yale University, New Haven, Conn.) was obtained and maintained on N agar. The plasmid libraries were transformed into CGSC #5408 by electroporation using the Bio-Rad Gene Pulser and the manufacturer's conditions. The cells were plated on minimal E agar (Vogel and Bonner, *J Biol. Chem.* 218:97–106 (1956) containing 100 mg/ml ampicillin and 0.4% casamino acids at a density of approximately 10,000,000 transformants/10 cm plate. Adenine prototrophs were recovered at a frequency of $1/6 \times 10^7$ from the pFL61 library. Plasmid DNA was isolated form the colony for sequence analysis. Purified plasmid DNA was shown to transform CGSC #5408 to purine prototrophy at high frequency. The purified plasmid complemented two additional *E. coli* purA mutants: ES4 (CGSC #4431; *E. coli* Genetics Stock Center, Yale University, New Haven, Conn.) and TX595 (CGSC #7039; *E. coli* Genetics Stock Center, Yale University, New Haven, Conn.), further confirming that it encoded a functional ADSS enzyme.

A restriction digest revealed that the cDNA insert was greater than 3 kB; sequence analysis revealed that the cDNA was chimeric, containing at the 3' end 1512 bp preceded by a poly A region. This 1512 bp region encodes an incomplete ADSS containing the mature protein sequence and a partial probable chloroplast transit peptide. A database search with the GAP program (Deveraux et al., *Nucleic Acids Res.* 12:387–395 (1984) reveals homology with the ADSS from *S. cerevisiae*. The two proteins are 70% similar, 51% identical with regions of high homology. The protein is 65% similar, 44% identical with *E. coli* ADSS.

ADSS-1, in the pBluescript SK vector, was deposited Sep. 22, 1994 as pWDC-6 (NRRL #B-21328).

The Arabidopsis cDNA sequence encoding ADSS-1 contained in pWDC-6 is set forth in SEQ ID NO:1. The ADSS-1 amino acid sequence encoded by this cDNA is set forth in SEQ ID NO:2.

Example 2

Isolation of Maize cDNAs encoding ADSS genes based on sequence homology to Arabidopsis ADSS.

A custom-made Unizap *Zea Mays* (cv. Blizzard) cDNA library was purchased from Clontech. Approximately 160,000 pfu of the phage library was plated at a density of 8,000 plaques per 10 cm Petri dish, and duplicate filter lifts were made onto nitrocellulose membrane (Scheiller and Scheull) after approximately 7 hours growth at 37°. The filter lifts were probed with a PCR amplified fragment of the Arabidopsis ADSS cDNA labeled with $^{32}$P-dCTP by the random priming method (Life Technologies, Bethesda, Md.). Hybridization and wash conditions were at 50° as described in Church and Gilbert, 1984. After purification to single positively hybridizing plaques, plasmids were in vivo excised and cDNA inserts sequenced using dideoxy terminators labeled with fluorescent dyes (Applied Biosystems, Inc., Foster City, Calif.). The sequence thus obtained for the maize ADSS cDNA and the protein it encodes are provided as SEQ ID NOS:3 and 4, respectively.

Example 3

Isolation of additional ADSS genes based on sequence homology to known ADSS coding sequences A phage or plasmid library is plated at a density of approximately 10,000 plaques on a 10 cm Petri dish, and filter lifts of the plaques are made after overnight growth of the plates at 37° C. The plaque lifts are probed with one of the cDNAs set forth in SEQ ID NOS:1 or 3, labeled with 32P-dCTP by the random priming method by means of a PrimeTime kit (International Biotechnologies, Inc., New Haven, Conn.). Hybridization conditions are 7% sodium dodecyl sulfate (SDS), 0.5M NaPO4 pH 7.0, 1 mM EDTA at 50° C. After hybridization overnight, the filters are washed with 2× SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain ADSS genes sequentially homologous to the known ADSS coding sequences from any other eukaryote, particularly other higher plant species.

An alignment of the predicted amino acid sequences of the respective proteins encoded by the nucleotide sequences shown in SEQ ID NOS:1 and 3 are set forth in Table 1.

TABLE 1

Comparison of the Arabidopsis (SEQ ID NO: 2) and Maize (SEQ ID NO: 4) ADSS-1 Amino Acid Sequences Identical residues are denoted by the vertical bar between the two sequences. Alignment is performed using the GAP program described in Deveraux *et al., Nucleic Acids Res. 12*:387–395 (1984).

```
  1 MSLSSLTLDSNPRFAVGGPYHRRYPPLHHPRSFVSCSAKRPAVSASLSVA  50 (SEQ ID NO: 2)
    ||||.|   |:|  |.:|. .. :|: . :.|.  ..|: |...|   |.
  1 MSLSTL...SHPAAAAAGSGKSLFPAGPAAQSVHFPKARLPVPAA...VS  44 (SEQ ID NO: 4)

 51 ADSAATESLGRIGSLSQVSGVLGCQWGDEGKGKLVDILAQHFDIVARCQG 100
    |..||... :|::||.|||||||:||||||||||||:||.:|||||||||
 45 AATAAVHAEDRVSSLTQVSGVLGSQWGDEGKGKLVDVLAPRFDIVARCQG  94

101 GANAGHTIYNSEGKKFALHLVPSGILNEDTTCVIGNGVVVHLPGLFKEID 150
    ||||||||||||||||||||||||||:|:| ||:|||.|:|:||:| |||
 95 GANAGHTIYNSEGKKFALHLVPSGILHEGTLCVVGNGAVIHVPGFFGEID 144

151 GLESNGVSCKGRILVSDRAHLLFDFHQEVDGLRESELAKSFIGTTKRGIG 200
    |||||||.| ||||||||||||||:||.||||||.||..|||||||||||
145 GLESNGVRCGGRILVSDRAHLLFDLHQAVDGLREAELENSFIGTTKRGIG 194

201 PAYSSKVIRNGIRVGDLRHMDTLPQKLDLLLSDAAARFQGFKYTPEMLRE 250
    |.|||||.|||:||.|||||||:.:|||:|:.|||.|||||.|...:|:|
195 PCYSSKVTRNGLRVCDLRHMDTFGDKLDILFKDAASRFQGFQYSKSLLKE 244

251 EVEAYKRYADRLEPYITDTVHFINDSISQKKKVLVEGGQATMLDIDFGTY 300
    ||| ||::||||||:|.||||.:|:||.||||:|||||||||||||||||
245 EVERYKKFADRLEPFIADTVHVLNESIKQKKKILVEGGQATMLDIDFGTY 294

301 PFVTSSSPSAGGICTGLGIAPSVVGDLIGVVKAYTTRVGSGPFPTENLGT 350
    |||||||||||||||||||||..:|||||||||||.|||||||||| :|.
295 PFVTSSSPSAGGICTGLGIAPRAIGDLIGVVKAYTSRVGSGPFPTELFGE 344

351 GGDLLRLAGQEFGTTTGRPRRCGWLDIVALKFSCQINGFASLNLTKLDVL 400
    :|| || || ||||||||||||||||||||| |||||||.||||||||||
345 EGDRLRKAGMEFGTTTGRPRRCGWLDIVALKHSCQINGFSSLNLTKLDVL 394
```

TABLE 1-continued

Comparison of the Arabidopsis (SEQ ID NO: 2) and Maize (SEQ ID NO: 4) ADSS-1 Amino Acid Sequences Identical residues are denoted by the vertical bar between the two sequences. Alignment is performed using the GAP program described in Deveraux *et al., Nucleic Acids Res. 12*:387–395 (1984).

```
401 SDLNEIQLGVAYKRSDGTPVKSFPGDLRLLEELHVEYEVLPGWKSDISSV 450
    |:|.||.:||.|...|| .:.||||||  ||:::|:||||||||.|||||
395 SGLSEIKVGVSYTQTDGQKLQSFPGDLDTLEQVQVNYEVLPGWQSDISSV 444

451 RNYSDLPKAAQQYVERIEELVGVPIHYIGIGPGRDALIYK* 491
    |.|.:||.||. ||||||||||||:||||:|||||||||||
445 RRYDELPQAARLYVERIEELVGVPVHYIGVGPGRDALIYK* 485
```

************************************************************

Various modifications of the invention described herein will become apparent to those skilled in the art. Such modifications are intended to fall within the scope of the appended claims.

We claim:

1. A nucleotide probe comprising a contiguous portion of at least 10 nucleotides in length of a coding sequence, or a complementary sequence thereto, for adenylosuccinate synthetase enzyme (ADSS) from Arabidopsis or maize, wherein said probe binds specifically to a plant adenylosuccinate synthetase gene or mRNA.

2. A method for detecting an ADSS gene or mRNA comprising combining the nucleotide probe of claim 1, with an unknown nucleotide sequence under conditions suitable for specific binding of said nucleotide probe to a plant adenylosuccinate synthetase gene or mRNA, and determining whether said nucleotide probe binds specifically to said unknown nucleotide seguence.

3. The method of claim 2, wherein said probe is derived from a plant ADSS coding sequence selected from the group consisting of Arabidopsis ADSS coding sequence set forth in SEQ ID No. 1, from nucleotide 1 to nucleotide 1471, and maize ADSS coding sequence set forth in SEQ ID No. 3, from nucleotide 18 to nucleotide 1469.

4. The method of claim 3 wherein the isolated DNA is that set forth in SEQ ID NO:1.

5. The method of claim 3 wherein the isolated DNA is that set forth in SEQ ID NO:3.

6. A method for detecting an ADSS gene or mRNA comprising combining a probe of at least 20 nucleotides in length of an isolated DNA molecule selected for the group consisting of Arab idops is ADSS coding sequence set for the in SEQ ID NO:1, from nucleotide 1 to nucleotide 1471, and maize ADSS coding sequence set forth in SEQ ID NO:3, from nucleotide 18 to nucleotide 1469, with an unknown sequence under conditions suitable for specific binding of said probe to a plant adenylosuccinate synthetase gene or mRNA, wherein said probe specifically hybridizes to a plant adenylosuccinate synthetase (ADSS) gene or mRNA after polymerase chain reaction, and determining whether said probe binds specifically to said unknown nucleotide sequence.

7. The method of claim 6 in which the isolated DNA is that set forth in SEQ ID NO:1.

8. The method of claim 6 in which the isolated DNA is that set forth in SEQ ID NO:3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1516 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i x ) FEATURE:
( A ) NAME/KEY: CDS
( B ) LOCATION: 1..1470
( D ) OTHER INFORMATION: /product= "Arabidopsis Adenylosuccinate Synthetase"

( x i ) SEQUENCE DESCRIPTION: SEQ ID NO:1:

```
ATG TCT CTC TCT TCC CTC ACT CTC GAC TCC AAT CCA AGA TTC GCT GTT     48
Met Ser Leu Ser Ser Leu Thr Leu Asp Ser Asn Pro Arg Phe Ala Val
  1               5                  10                  15

GGT GGA CCT TAT CAC CGC CGT TAT CCT CCT CTT CAC CAC CCT CGA AGC     96
Gly Gly Pro Tyr His Arg Arg Tyr Pro Pro Leu His His Pro Arg Ser
             20                  25                  30

TTC GTC TCT TGC TCT GCT AAA CGT CCA GCT GTC TCC GCT TCA CTG AGC    144
Phe Val Ser Cys Ser Ala Lys Arg Pro Ala Val Ser Ala Ser Leu Ser
         35                  40                  45

GTC GCC GCT GAT TCA GCC GCC ACT GAG TCT CTT GGA CGG ATT GGA TCA    192
Val Ala Ala Asp Ser Ala Ala Thr Glu Ser Leu Gly Arg Ile Gly Ser
     50                  55                  60

CTG AGT CAA GTA TCT GGT GTA CTC GGT TGC CAA TGG GGA GAT GAA GGT    240
Leu Ser Gln Val Ser Gly Val Leu Gly Cys Gln Trp Gly Asp Glu Gly
 65                  70                  75                  80

AAA GGC AAA CTC GTT GAC ATC TTA GCC CAA CAC TTT GAC ATC GTT GCT    288
Lys Gly Lys Leu Val Asp Ile Leu Ala Gln His Phe Asp Ile Val Ala
                 85                  90                  95

CGT TGT CAG GGT GGA GCT AAT GCT GGA CAC ACT ATA TAC AAT TCA GAG    336
```

-continued

```
Arg Cys Gln Gly Gly Ala Asn Ala Gly His Thr Ile Tyr Asn Ser Glu
            100                 105                 110

GGA AAG AAA TTT GCA CTT CAC CTT GTG CCT TCA GGT ATC CTG AAT GAG   384
Gly Lys Lys Phe Ala Leu His Leu Val Pro Ser Gly Ile Leu Asn Glu
        115                 120                 125

GAT ACT ACT TGT GTC ATT GGA AAC GGA GTT GTG GTG CAT TTG CCA GGT   432
Asp Thr Thr Cys Val Ile Gly Asn Gly Val Val Val His Leu Pro Gly
    130                 135                 140

CTC TTC AAA GAG ATT GAT GGT TTG GAG TCC AAT GGT GTC TCC TGT AAA   480
Leu Phe Lys Glu Ile Asp Gly Leu Glu Ser Asn Gly Val Ser Cys Lys
145                 150                 155                 160

GGA AGG ATT TTG GTC TCT GAT CGC GCT CAC TTG TTA TTC GAT TTC CAT   528
Gly Arg Ile Leu Val Ser Asp Arg Ala His Leu Leu Phe Asp Phe His
                165                 170                 175

CAA GAG GTT GAT GGG CTC AGG GAA TCT GAG CTT GCC AAG TCG TTC ATT   576
Gln Glu Val Asp Gly Leu Arg Glu Ser Glu Leu Ala Lys Ser Phe Ile
            180                 185                 190

GGC ACC ACC AAG AGG GGA ATT GGT CCT GCC TAC TCT AGT AAA GTG ATA   624
Gly Thr Thr Lys Arg Gly Ile Gly Pro Ala Tyr Ser Ser Lys Val Ile
        195                 200                 205

AGG AAT GGT ATT AGA GTA GGT GAT CTC AGG CAC ATG GAT ACT TTA CCT   672
Arg Asn Gly Ile Arg Val Gly Asp Leu Arg His Met Asp Thr Leu Pro
    210                 215                 220

CAA AAG CTT GAC CTT TTA CTA TCA GAT GCA GCG GCA AGG TTT CAA GGG   720
Gln Lys Leu Asp Leu Leu Leu Ser Asp Ala Ala Ala Arg Phe Gln Gly
225                 230                 235                 240

TTC AAG TAT ACT CCT GAA ATG CTT CGG GAA GAA GTT GAA GCA TAC AAG   768
Phe Lys Tyr Thr Pro Glu Met Leu Arg Glu Glu Val Glu Ala Tyr Lys
                245                 250                 255

AGA TAC GCT GAC AGA TTG GAG CCC TAC ATT ACT GAC ACT GTC CAT TTC   816
Arg Tyr Ala Asp Arg Leu Glu Pro Tyr Ile Thr Asp Thr Val His Phe
            260                 265                 270

ATC AAT GAC TCG ATT TCG CAG AAG AAA AAG GTT TTG GTC GAA GGT GGT   864
Ile Asn Asp Ser Ile Ser Gln Lys Lys Lys Val Leu Val Glu Gly Gly
        275                 280                 285

CAA GCT ACA ATG TTG GAC ATT GAC TTT GGG ACT TAT CCT TTT GTT ACT   912
Gln Ala Thr Met Leu Asp Ile Asp Phe Gly Thr Tyr Pro Phe Val Thr
    290                 295                 300

TCC TCC AGC CCC TCA GCC GGT GGG ATC TGC ACA GGT CTT GGT ATT GCA   960
Ser Ser Ser Pro Ser Ala Gly Gly Ile Cys Thr Gly Leu Gly Ile Ala
305                 310                 315                 320

CCA AGT GTT GTT GGT GAT CTA ATT GGA GTG GTA AAA GCA TAC ACT ACA  1008
Pro Ser Val Val Gly Asp Leu Ile Gly Val Val Lys Ala Tyr Thr Thr
                325                 330                 335

AGA GTT GGT TCA GGT CCA TTC CCG ACA GAA AAT TTG GGC ACA GGT GGT  1056
Arg Val Gly Ser Gly Pro Phe Pro Thr Glu Asn Leu Gly Thr Gly Gly
            340                 345                 350

GAC CTT CTT AGG TTA GCT GGA CAG GAG TTT GGC ACT ACA ACT GGT CGT  1104
Asp Leu Leu Arg Leu Ala Gly Gln Glu Phe Gly Thr Thr Thr Gly Arg
        355                 360                 365

CCT CGT CGG TGT GGC TGG CTT GAC ATT GTT GCC CTG AAA TTT TCT TGC  1152
Pro Arg Arg Cys Gly Trp Leu Asp Ile Val Ala Leu Lys Phe Ser Cys
    370                 375                 380

CAA ATC AAT GGA TTT GCA TCA CTT AAT CTC ACT AAG CTT GAT GTA CTT  1200
Gln Ile Asn Gly Phe Ala Ser Leu Asn Leu Thr Lys Leu Asp Val Leu
385                 390                 395                 400

TCG GAT CTG AAC GAA ATC CAG CTG GGT GTG GCT TAC AAG AGG AGT GAC  1248
Ser Asp Leu Asn Glu Ile Gln Leu Gly Val Ala Tyr Lys Arg Ser Asp
                405                 410                 415

GGC ACC CCT GTT AAA TCA TTC CCT GGT GAT CTT CGT CTT CTC GAA GAA  1296
```

-continued

Gly Thr Pro Val Lys Ser Phe Pro Gly Asp Leu Arg Leu Leu Glu Glu
420 425 430

CTG CAT GTG GAG TAT GAA GTC TTA CCT GGG TGG AAG TCT GAC ATA TCC 1344
Leu His Val Glu Tyr Glu Val Leu Pro Gly Trp Lys Ser Asp Ile Ser
435 440 445

TCG GTC AGA AAC TAC TCT GAT CTT CCA AAG GCT GCT CAG CAA TAT GTT 1392
Ser Val Arg Asn Tyr Ser Asp Leu Pro Lys Ala Ala Gln Gln Tyr Val
450 455 460

GAG AGG ATT GAA GAA CTC GTG GGT GTG CCC ATT CAT TAC ATT GGT ATT 1440
Glu Arg Ile Glu Glu Leu Val Gly Val Pro Ile His Tyr Ile Gly Ile
465 470 475 480

GGG CCC GGT CGT GAT GCC CTT ATA TAT AAA TGATTTTTAG TGTTAGGCTT 1490
Gly Pro Gly Arg Asp Ala Leu Ile Tyr Lys
485 490

TTTTGGTTCC TCCACAAACT CAAAAT 1516

( 2 ) INFORMATION FOR SEQ ID NO:2:

( i ) SEQUENCE CHARACTERISTICS:
( A ) LENGTH: 490 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ser Leu Ser Ser Leu Thr Leu Asp Ser Asn Pro Arg Phe Ala Val
1 5 10 15

Gly Gly Pro Tyr His Arg Arg Tyr Pro Pro Leu His His Pro Arg Ser
20 25 30

Phe Val Ser Cys Ser Ala Lys Arg Pro Ala Val Ser Ala Ser Leu Ser
35 40 45

Val Ala Ala Asp Ser Ala Ala Thr Glu Ser Leu Gly Arg Ile Gly Ser
50 55 60

Leu Ser Gln Val Ser Gly Val Leu Gly Cys Gln Trp Gly Asp Glu Gly
65 70 75 80

Lys Gly Lys Leu Val Asp Ile Leu Ala Gln His Phe Asp Ile Val Ala
85 90 95

Arg Cys Gln Gly Gly Ala Asn Ala Gly His Thr Ile Tyr Asn Ser Glu
100 105 110

Gly Lys Lys Phe Ala Leu His Leu Val Pro Ser Gly Ile Leu Asn Glu
115 120 125

Asp Thr Thr Cys Val Ile Gly Asn Gly Val Val Val His Leu Pro Gly
130 135 140

Leu Phe Lys Glu Ile Asp Gly Leu Glu Ser Asn Gly Val Ser Cys Lys
145 150 155 160

Gly Arg Ile Leu Val Ser Asp Arg Ala His Leu Leu Phe Asp Phe His
165 170 175

Gln Glu Val Asp Gly Leu Arg Glu Ser Glu Leu Ala Lys Ser Phe Ile
180 185 190

Gly Thr Thr Lys Arg Gly Ile Gly Pro Ala Tyr Ser Ser Lys Val Ile
195 200 205

Arg Asn Gly Ile Arg Val Gly Asp Leu Arg His Met Asp Thr Leu Pro
210 215 220

Gln Lys Leu Asp Leu Leu Leu Ser Asp Ala Ala Ala Arg Phe Gln Gly
225 230 235 240

Phe Lys Tyr Thr Pro Glu Met Leu Arg Glu Glu Val Glu Ala Tyr Lys
245 250 255

-continued

Arg Tyr Ala Asp Arg Leu Glu Pro Tyr Ile Thr Asp Thr Val His Phe
260 265 270

Ile Asn Asp Ser Ile Ser Gln Lys Lys Lys Val Leu Val Glu Gly Gly
275 280 285

Gln Ala Thr Met Leu Asp Ile Asp Phe Gly Thr Tyr Pro Phe Val Thr
290 295 300

Ser Ser Ser Pro Ser Ala Gly Gly Ile Cys Thr Gly Leu Gly Ile Ala
305 310 315 320

Pro Ser Val Val Gly Asp Leu Ile Gly Val Val Lys Ala Tyr Thr Thr
325 330 335

Arg Val Gly Ser Gly Pro Phe Pro Thr Glu Asn Leu Gly Thr Gly Gly
340 345 350

Asp Leu Leu Arg Leu Ala Gly Gln Glu Phe Gly Thr Thr Thr Gly Arg
355 360 365

Pro Arg Arg Cys Gly Trp Leu Asp Ile Val Ala Leu Lys Phe Ser Cys
370 375 380

Gln Ile Asn Gly Phe Ala Ser Leu Asn Leu Thr Lys Leu Asp Val Leu
385 390 395 400

Ser Asp Leu Asn Glu Ile Gln Leu Gly Val Ala Tyr Lys Arg Ser Asp
405 410 415

Gly Thr Pro Val Lys Ser Phe Pro Gly Asp Leu Arg Leu Leu Glu Glu
420 425 430

Leu His Val Glu Tyr Glu Val Leu Pro Gly Trp Lys Ser Asp Ile Ser
435 440 445

Ser Val Arg Asn Tyr Ser Asp Leu Pro Lys Ala Ala Gln Gln Tyr Val
450 455 460

Glu Arg Ile Glu Glu Leu Val Gly Val Pro Ile His Tyr Ile Gly Ile
465 470 475 480

Gly Pro Gly Arg Asp Ala Leu Ile Tyr Lys
485 490

( 2 ) INFORMATION FOR SEQ ID NO:3:

( i ) SEQUENCE CHARACTERISTICS:
( A ) LENGTH: 1835 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i x ) FEATURE:
( A ) NAME/KEY: CDS
( B ) LOCATION: 18..1469
( D ) OTHER INFORMATION: /product= "Maize Adenylosuccinate Synthetase"

( x i ) SEQUENCE DESCRIPTION: SEQ ID NO:3:

AAAACCCTCC CACCATC ATG TCG CTC TCC ACA CTC AGC CAC CCG GCC GCC 50
Met Ser Leu Ser Thr Leu Ser His Pro Ala Ala
495 500

GCC GCC GCC GGG AGC GGA AAA TCC CTT TTC CCG GCT GGC CCG GCG GCG 98
Ala Ala Ala Gly Ser Gly Lys Ser Leu Phe Pro Ala Gly Pro Ala Ala
505 510 515

CAG TCC GTA CAT TTC CCC AAG GCA CGG CTC CCT GTC CCC GCC GCC GTC 146
Gln Ser Val His Phe Pro Lys Ala Arg Leu Pro Val Pro Ala Ala Val
520 525 530

TCC GCC GCT ACT GCG GCT GTT CAC GCG GAG GAT AGG GTT TCG TCG CTG 194

-continued

```
Ser Ala Ala Thr Ala Ala Val His Ala Glu Asp Arg Val Ser Ser Leu
    535                 540                 545

ACT CAA GTC TCC GGC GTG CTG GGG TCG CAG TGG GGC GAC GAG GGA AAG     242
Thr Gln Val Ser Gly Val Leu Gly Ser Gln Trp Gly Asp Glu Gly Lys
550                 555                 560                 565

GGC AAG CTC GTC GAC GTG CTC GCC CCC CGC TTC GAC ATA GTC GCG CGT     290
Gly Lys Leu Val Asp Val Leu Ala Pro Arg Phe Asp Ile Val Ala Arg
                570                 575                 580

TGC CAG GGG GGA GCG AAC GCT GGA CAT ACC ATC TAC AAC TCA GAA GGC     338
Cys Gln Gly Gly Ala Asn Ala Gly His Thr Ile Tyr Asn Ser Glu Gly
            585                 590                 595

AAG AAG TTT GCT CTG CAT CTT GTT CCA TCT GGT ATT CTC CAT GAA GGG     386
Lys Lys Phe Ala Leu His Leu Val Pro Ser Gly Ile Leu His Glu Gly
        600                 605                 610

ACA CTG TGT GTT GTT GGC AAT GGA GCA GTC ATC CAT GTT CCA GGG TTC     434
Thr Leu Cys Val Val Gly Asn Gly Ala Val Ile His Val Pro Gly Phe
    615                 620                 625

TTT GGA GAA ATT GAT GGT CTT GAG TCC AAT GGA GTC CGC TGC GGT GGA     482
Phe Gly Glu Ile Asp Gly Leu Glu Ser Asn Gly Val Arg Cys Gly Gly
630                 635                 640                 645

AGG ATA CTG GTA TCC GAC CGG GCA CAT CTG CTG TTT GAT CTG CAC CAG     530
Arg Ile Leu Val Ser Asp Arg Ala His Leu Leu Phe Asp Leu His Gln
                650                 655                 660

GCT GTG GAT GGA CTT AGG GAA GCA GAG CTT GAA AAT TCA TTT ATA GGG     578
Ala Val Asp Gly Leu Arg Glu Ala Glu Leu Glu Asn Ser Phe Ile Gly
            665                 670                 675

ACA ACT AAG AGA GGC ATT GGT CCT TGT TAC TCC AGC AAG GTA ACT CGA     626
Thr Thr Lys Arg Gly Ile Gly Pro Cys Tyr Ser Ser Lys Val Thr Arg
        680                 685                 690

AAT GGA CTG CGG GTT TGT GAT TTA CGA CAC ATG GAC ACT TTT GGG GAT     674
Asn Gly Leu Arg Val Cys Asp Leu Arg His Met Asp Thr Phe Gly Asp
    695                 700                 705

AAG CTT GAC ATC TTA TTC AAA GAC GCT GCT TCG AGA TTT CAA GGC TTT     722
Lys Leu Asp Ile Leu Phe Lys Asp Ala Ala Ser Arg Phe Gln Gly Phe
710                 715                 720                 725

CAG TAC AGC AAA AGC TTG CTC AAG GAA GAG GTT GAG AGA TAC AAG AAG     770
Gln Tyr Ser Lys Ser Leu Leu Lys Glu Glu Val Glu Arg Tyr Lys Lys
                730                 735                 740

TTT GCT GAT CGC TTG GAG CCC TTC ATT GCT GAT ACC GTG CAT GTG CTA     818
Phe Ala Asp Arg Leu Glu Pro Phe Ile Ala Asp Thr Val His Val Leu
            745                 750                 755

AAT GAA TCT ATC AAG CAG AAG AAG AAA ATC CTG GTC GAA GGC GGC CAA     866
Asn Glu Ser Ile Lys Gln Lys Lys Lys Ile Leu Val Glu Gly Gly Gln
        760                 765                 770

GCA ACT ATG CTG GAT ATT GAT TTT GGC ACT TAT CCA TTT GTG ACT TCT     914
Ala Thr Met Leu Asp Ile Asp Phe Gly Thr Tyr Pro Phe Val Thr Ser
    775                 780                 785

TCT AGC CCT TCA GCT GGC GGG ATA TGC ACA GGC CTA GGG ATT GCT CCA     962
Ser Ser Pro Ser Ala Gly Gly Ile Cys Thr Gly Leu Gly Ile Ala Pro
790                 795                 800                 805

AGG GCA ATT GGC GAC CTG ATT GGA GTG GTC AAA GCT TAC ACA TCT AGA    1010
Arg Ala Ile Gly Asp Leu Ile Gly Val Val Lys Ala Tyr Thr Ser Arg
                810                 815                 820

GTC GGC TCT GGC CCT TTC CCA ACT GAA CTA TTT GGA GAG GAA GGT GAT    1058
Val Gly Ser Gly Pro Phe Pro Thr Glu Leu Phe Gly Glu Glu Gly Asp
            825                 830                 835

CGC CTT AGG AAA GCT GGA ATG GAA TTT GGC ACA ACA ACA GGT CGC CCA    1106
Arg Leu Arg Lys Ala Gly Met Glu Phe Gly Thr Thr Thr Gly Arg Pro
        840                 845                 850

AGG CGT TGC GGC TGG CTT GAC ATT GTT GCG CTT AAG CAC AGC TGC CAA    1154
```

-continued

```
Arg Arg Cys Gly Trp Leu Asp Ile Val Ala Leu Lys His Ser Cys Gln
    855                 860                 865

ATC AAT GGG TTC TCA TCA CTT AAT CTG ACC AAA CTG GAT GTT CTG TCC      1202
Ile Asn Gly Phe Ser Ser Leu Asn Leu Thr Lys Leu Asp Val Leu Ser
870                 875                 880                 885

GGG TTG TCA GAA ATT AAG GTG GGT GTT TCT TAT ACC CAG ACT GAT GGA      1250
Gly Leu Ser Glu Ile Lys Val Gly Val Ser Tyr Thr Gln Thr Asp Gly
                890                 895                 900

CAG AAG CTG CAA TCC TTC CCT GGG GAT CTT GAT ACC CTT GAG CAA GTA      1298
Gln Lys Leu Gln Ser Phe Pro Gly Asp Leu Asp Thr Leu Glu Gln Val
            905                 910                 915

CAG GTC AAC TAT GAG GTT CTG CCT GGG TGG CAA AGT GAC ATT TCT TCT      1346
Gln Val Asn Tyr Glu Val Leu Pro Gly Trp Gln Ser Asp Ile Ser Ser
        920                 925                 930

GTT CGA AGA TAC GAT GAA CTT CCC CAA GCT GCC CGC CTC TAT GTG GAG      1394
Val Arg Arg Tyr Asp Glu Leu Pro Gln Ala Ala Arg Leu Tyr Val Glu
    935                 940                 945

AGG ATA GAA GAA CTT GTT GGT GTT CCC GTG CAC TAC ATT GGT GTT GGA      1442
Arg Ile Glu Glu Leu Val Gly Val Pro Val His Tyr Ile Gly Val Gly
950                 955                 960                 965

CCT GGC AGA GAT GCT CTC ATA TAC AAG TAAAAGCAAC TTTATTTGGT           1489
Pro Gly Arg Asp Ala Leu Ile Tyr Lys
                970

CCTTGGTTGG GCGGAAACCT GGCCGGGACT CGGGAGCATT TGCATTTTCT TGGCGTGGTA    1549

GCTTTTGATA CGGTGAAGTC ACTGACTCGT GGAGTGATGT TGCTCAATAA TCAGAACCTT    1609

GTTCTAATAC AGCCGCTGAG ACATCAGCTA AGGCGAATAA GGGAAGGATG AGTCATTTGC    1669

ACCATGTTTG ACCACCAATT GTTAGGTGGT CCATATATTT TGTACTAATT GTGAGACTTT    1729

GTGCTATGGA TCTCAACTGT ATACCTTGCT GGTGCATGGC TTTGGGTTTA CATGGTTGAA    1789

AATGAGATTG GTGTACTAAT TGTCTAAAAA AAAAAAAAAA AAAAAA                   1835
```

( 2 ) INFORMATION FOR SEQ ID NO:4:

( i ) SEQUENCE CHARACTERISTICS:
( A ) LENGTH: 484 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Ser Leu Ser Thr Leu Ser His Pro Ala Ala Ala Ala Ala Gly Ser
  1               5                  10                  15

Gly Lys Ser Leu Phe Pro Ala Gly Pro Ala Ala Gln Ser Val His Phe
             20                  25                  30

Pro Lys Ala Arg Leu Pro Val Pro Ala Ala Val Ser Ala Ala Thr Ala
         35                  40                  45

Ala Val His Ala Glu Asp Arg Val Ser Ser Leu Thr Gln Val Ser Gly
     50                  55                  60

Val Leu Gly Ser Gln Trp Gly Asp Glu Gly Lys Gly Lys Leu Val Asp
 65                  70                  75                  80

Val Leu Ala Pro Arg Phe Asp Ile Val Ala Arg Cys Gln Gly Gly Ala
                 85                  90                  95

Asn Ala Gly His Thr Ile Tyr Asn Ser Glu Gly Lys Lys Phe Ala Leu
            100                 105                 110

His Leu Val Pro Ser Gly Ile Leu His Glu Gly Thr Leu Cys Val Val
        115                 120                 125

Gly Asn Gly Ala Val Ile His Val Pro Gly Phe Phe Gly Glu Ile Asp
```

-continued

| | | | | | | | | | | | | | | | |
|---|---|---|---|---|---|---|---|---|---|---|---|---|---|---|---|
| | 130 | | | | | 135 | | | | | 140 | | | | |
| Gly | Leu | Glu | Ser | Asn | Gly | Val | Arg | Cys | Gly | Gly | Arg | Ile | Leu | Val | Ser |
| 145 | | | | | 150 | | | | | 155 | | | | | 160 |
| Asp | Arg | Ala | His | Leu | Leu | Phe | Asp | Leu | His | Gln | Ala | Val | Asp | Gly | Leu |
| | | | | 165 | | | | | 170 | | | | | 175 | |
| Arg | Glu | Ala | Glu | Leu | Glu | Asn | Ser | Phe | Ile | Gly | Thr | Thr | Lys | Arg | Gly |
| | | | 180 | | | | | 185 | | | | | 190 | | |
| Ile | Gly | Pro | Cys | Tyr | Ser | Ser | Lys | Val | Thr | Arg | Asn | Gly | Leu | Arg | Val |
| | | 195 | | | | | 200 | | | | | 205 | | | |
| Cys | Asp | Leu | Arg | His | Met | Asp | Thr | Phe | Gly | Asp | Lys | Leu | Asp | Ile | Leu |
| | 210 | | | | | 215 | | | | | 220 | | | | |
| Phe | Lys | Asp | Ala | Ala | Ser | Arg | Phe | Gln | Gly | Phe | Gln | Tyr | Ser | Lys | Ser |
| 225 | | | | | 230 | | | | | 235 | | | | | 240 |
| Leu | Leu | Lys | Glu | Glu | Val | Glu | Arg | Tyr | Lys | Lys | Phe | Ala | Asp | Arg | Leu |
| | | | | 245 | | | | | 250 | | | | | 255 | |
| Glu | Pro | Phe | Ile | Ala | Asp | Thr | Val | His | Val | Leu | Asn | Glu | Ser | Ile | Lys |
| | | | 260 | | | | | 265 | | | | | 270 | | |
| Gln | Lys | Lys | Lys | Ile | Leu | Val | Glu | Gly | Gly | Gln | Ala | Thr | Met | Leu | Asp |
| | | 275 | | | | | 280 | | | | | 285 | | | |
| Ile | Asp | Phe | Gly | Thr | Tyr | Pro | Phe | Val | Thr | Ser | Ser | Ser | Pro | Ser | Ala |
| | 290 | | | | | 295 | | | | | 300 | | | | |
| Gly | Gly | Ile | Cys | Thr | Gly | Leu | Gly | Ile | Ala | Pro | Arg | Ala | Ile | Gly | Asp |
| 305 | | | | | 310 | | | | | 315 | | | | | 320 |
| Leu | Ile | Gly | Val | Val | Lys | Ala | Tyr | Thr | Ser | Arg | Val | Gly | Ser | Gly | Pro |
| | | | | 325 | | | | | 330 | | | | | 335 | |
| Phe | Pro | Thr | Glu | Leu | Phe | Gly | Glu | Glu | Gly | Asp | Arg | Leu | Arg | Lys | Ala |
| | | | 340 | | | | | 345 | | | | | 350 | | |
| Gly | Met | Glu | Phe | Gly | Thr | Thr | Thr | Gly | Arg | Pro | Arg | Arg | Cys | Gly | Trp |
| | | 355 | | | | | 360 | | | | | 365 | | | |
| Leu | Asp | Ile | Val | Ala | Leu | Lys | His | Ser | Cys | Gln | Ile | Asn | Gly | Phe | Ser |
| | 370 | | | | | 375 | | | | | 380 | | | | |
| Ser | Leu | Asn | Leu | Thr | Lys | Leu | Asp | Val | Leu | Ser | Gly | Leu | Ser | Glu | Ile |
| 385 | | | | | 390 | | | | | 395 | | | | | 400 |
| Lys | Val | Gly | Val | Ser | Tyr | Thr | Gln | Thr | Asp | Gly | Gln | Lys | Leu | Gln | Ser |
| | | | | 405 | | | | | 410 | | | | | 415 | |
| Phe | Pro | Gly | Asp | Leu | Asp | Thr | Leu | Glu | Gln | Val | Gln | Val | Asn | Tyr | Glu |
| | | | 420 | | | | | 425 | | | | | 430 | | |
| Val | Leu | Pro | Gly | Trp | Gln | Ser | Asp | Ile | Ser | Ser | Val | Arg | Arg | Tyr | Asp |
| | | 435 | | | | | 440 | | | | | 445 | | | |
| Glu | Leu | Pro | Gln | Ala | Ala | Arg | Leu | Tyr | Val | Glu | Arg | Ile | Glu | Glu | Leu |
| | 450 | | | | | 455 | | | | | 460 | | | | |
| Val | Gly | Val | Pro | Val | His | Tyr | Ile | Gly | Val | Gly | Pro | Gly | Arg | Asp | Ala |
| 465 | | | | | 470 | | | | | 475 | | | | | 480 |
| Leu | Ile | Tyr | Lys | | | | | | | | | | | | |